US 6,592,223 B1

(12) United States Patent
Stern et al.

(10) Patent No.: US 6,592,223 B1
(45) Date of Patent: Jul. 15, 2003

(54) SYSTEM AND METHOD FOR OPTIMAL VIEWING OF COMPUTER MONITORS TO MINIMIZE EYESTRAIN

(75) Inventors: Roger A. Stern, Cupertino, CA (US); Jory E. Moon, Los Altos, CA (US); Sherwyne R. Bakar, Palo Alto, CA (US)

(73) Assignee: Panaseca, Inc., Mountain View, CA (US)

( * ) Notice: Subject to any disclaimer, the term of this patent is extended or adjusted under 35 U.S.C. 154(b) by 0 days.

(21) Appl. No.: 09/680,573

(22) Filed: Oct. 6, 2000

Related U.S. Application Data

(60) Provisional application No. 60/158,586, filed on Oct. 7, 1999, and provisional application No. 60/222,268, filed on Jul. 31, 2000.

(51) Int. Cl.[7] .................................................. A61B 3/02
(52) U.S. Cl. ....................................................... 351/239
(58) Field of Search ................................. 351/205, 206, 351/208, 223, 237, 239, 242, 243, 245, 246; 396/2, 429; 348/552; 345/419

(56) References Cited

U.S. PATENT DOCUMENTS

| 5,121,981 | A | * | 6/1992 | Waltuck et al. | 351/243 |
| 5,367,614 | A | * | 11/1994 | Bisey | 345/419 |
| 5,668,743 | A | * | 9/1997 | Kushelvesky | 351/208 |
| 5,777,720 | A | * | 7/1998 | Shapiro et al. | 351/237 |
| 6,244,711 | B1 | * | 6/2001 | Fateh et al. | 351/208 |

* cited by examiner

Primary Examiner—George Manuel
(74) Attorney, Agent, or Firm—Robins & Pasternak LLP

(57) ABSTRACT

A system and method for helping ensure that a user of a computer is set up to optimally view the computer monitor under optimal conditions in order to minimize eyestrain. The system includes determining an optimal viewing distance and monitoring the distance of a user from the computer monitor during use of the computer. The system further includes notifying the user when they stray from the optimal viewing distance and further may include testing various aspects of the user's eyesight during use of the computer monitor.

45 Claims, 4 Drawing Sheets

# SYSTEM AND METHOD FOR OPTIMAL VIEWING OF COMPUTER MONITORS TO MINIMIZE EYESTRAIN

This application claims priority from U.S. Provisional Patent Application No. 60/158,586, filed Oct. 7, 1999 and U.S. Provisional Patent Application No.60/222,268, filed Jul. 31, 2000, the disclosures of which are incorporated herein by reference in their entirety for all purposes.

BACKGROUND OF THE INVENTION

1. Field of the Invention

The present invention relates to systems and methods for helping ensure that a user of a computer is properly positioned to view a monitor, and more particularly, to systems and methods for helping ensure that a user of a computer is set up to optimally view the computer monitor under optimal conditions.

2. Description of the Prior Art

A common problem of many computer users is that they often sit too close to the computer monitor. This is especially true of young children. It is well known that if one sits too close to the computer monitor, the eye will intently focus on what is many times a stationary image. This can lead to eyestrain.

Additionally, many users sit too long in front of a computer without taking a break. This is true for many workers who must operate a computer for almost the entire work day. It is often difficult to ascertain when one has spent too much time in front of a computer without taking a break. Additionally, many times the lighting in the room where the computer is located may not be optimal. This may lead to glare and other problems that also result in eyestrain.

Recent medical literature clearly shows an increase in eyestrain-related problems to computer users. Use of computers is rapidly growing among children and improper use of computers is thought to be a contributing factor to the increase in eyestrain related problems in children.

SUMMARY OF THE INVENTION

In accordance with one embodiment of the present invention, a user of a computer monitor determines a proper viewing distance. This may be accomplished by an installation program that will ask the user to select a viewing distance by displaying any one of a number of standard test patterns and asking the user to identify them. The optimal viewing distance would then be selected based upon the identification of the test patterns and would preferably be slightly closer than the farthest distance at which the user can correctly identify the test pattern.

In accordance with another embodiment of the present invention, the user will be notified when he is not at the proper viewing distance. This may be accomplished by switching the computer monitor's display to a "screensaver" type program, sounding an alarm, or even turning off the computer monitor. A sensor may be provided for monitoring the actual distance of the user. Preferably, the electrical interface to the sensor would be "piggybacked" onto an existing device, such as, for example, a keyboard or mouse, thus not requiring any additional computer resources or requiring any other source of electrical power.

In accordance with another embodiment of the present invention, statistics about a user's viewing distance are recorded. This may be especially useful in work situations where almost continuous use of the computer is anticipated. For example, there might be trend toward closer viewing as the length of time the computer is being used increases. In such a situation, this may indicate that a break is in order, and in a preferred embodiment of the present invention, the system would so notify the user.

In accordance with another embodiment of the present invention, the measured viewing distance may be used for a periodic test of the user's eyesight. For example, test patterns may be displayed and the user may be "scored" at some predetermined fixed distance. If the user scores too low on the tests, use of the computer may be inhibited.

In accordance with another embodiment of the present invention, the level of ambient light in the user's environment may be measured and suggestions may be provided by the system to either increase or decrease the amount of ambient light. In such an embodiment, a light level sensor may be incorporated into the system that would feed information regarding the ambient light into the computer through the shared interface as previously discussed.

In accordance with yet another embodiment of the present invention, the system may determine "amplitude of accommodation," which is the minimum distance between the eye and a viewing surface below which the surface is blurry.

In accordance with yet another embodiment of the present invention, a user may be presented with color tests and asked to respond to them. This may be done over a period of time to determine the user's interpretation of colors as use of the computer over the period of time progresses.

In yet another embodiment of the present invention, the system monitors the number of times or rate at which an individual blinks their eyes. The individual may be viewing a monitor and with a sensor or camera, the rate of blinking of the eyes is monitored. By monitoring the rate at which the individual blinks their eyes, or by monitoring the rate of changes in a baseline eye blink rate, early detection of eye irritation and visual fatigue is possible.

Other features and advantages of the present invention will be understood upon reading and understanding the detailed description of the preferred exemplary embodiments found herein below, in conjunction with reference to the drawings, in which like numerals represent like elements.

DETAILED DESCRIPTION OF THE PREFERRED EXEMPLARY EMBODIMENTS

Figure 1:
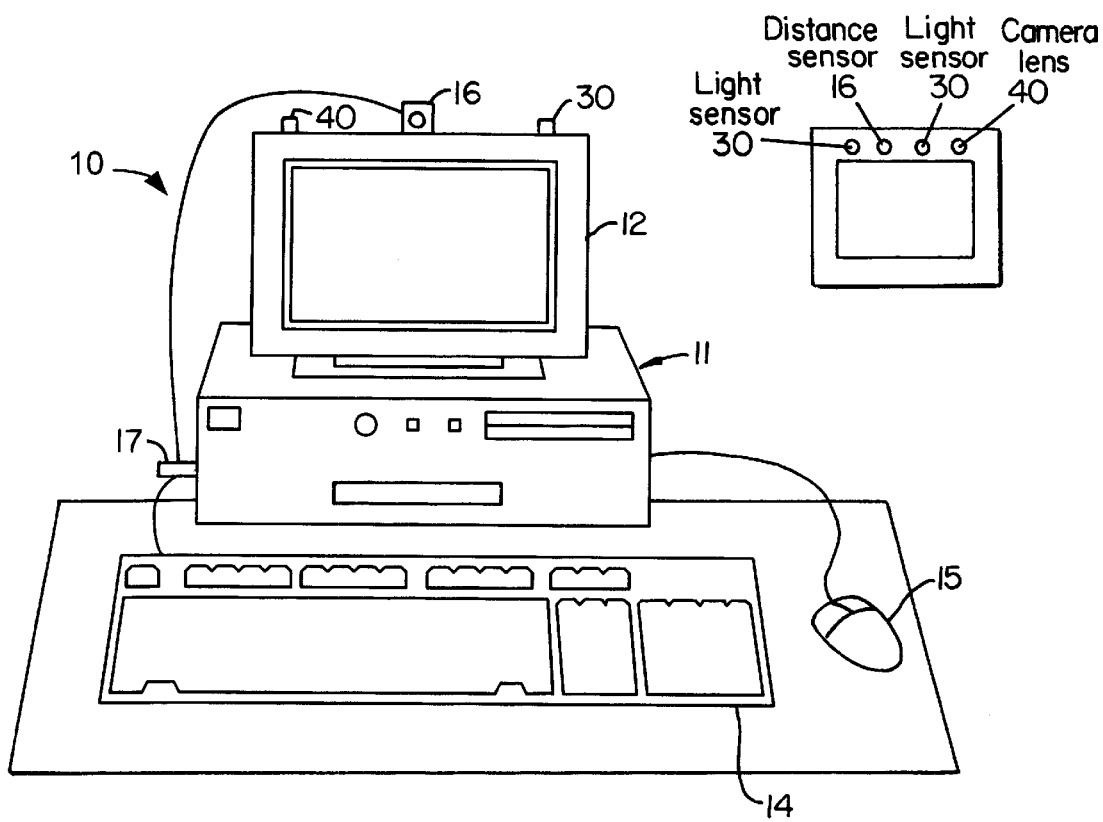
FIG. 1 is a schematic illustration of a system in accordance with the present invention with a computer system.
Figure 2:
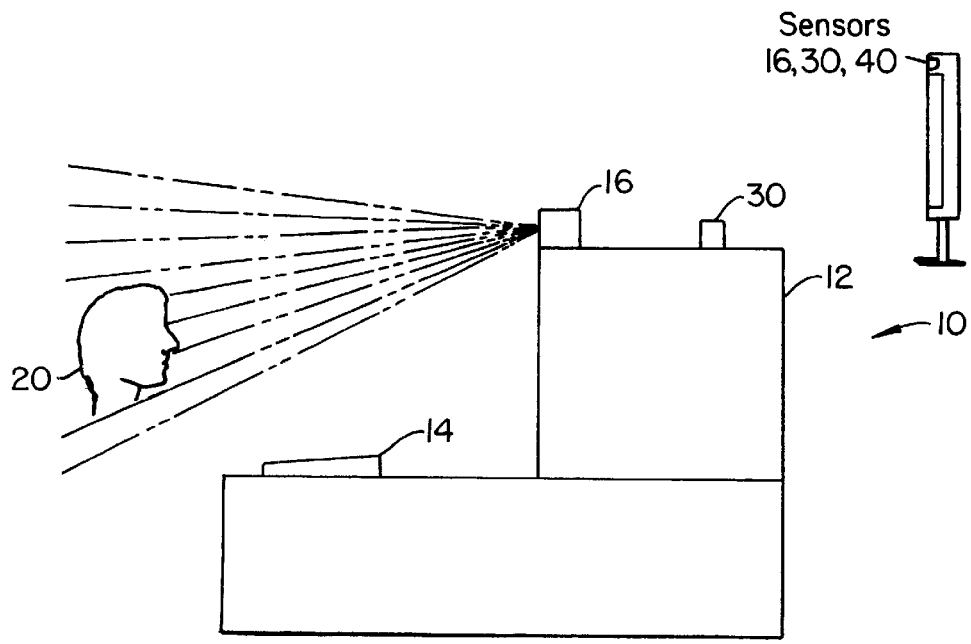
FIG. 2 is a side view of the system illustrated in FIG. 1.

FIGS. 1 and 2 schematically illustrate a possible arrangement of a system 10 in accordance with the present invention. System 10 is depicted as a computer system 11 including a computer monitor 12. Those skilled in the art will understand that other monitors will also benefit from the methods and system of the present invention. However, for simplicity and clarity, a computer system will be used to describe the present invention.

System 10 further includes computer inputs, such as, for example keyboard 14 and mouse 15. System 10 further includes at least one distance sensor 16. Preferably, the electrical interface to distance sensor 16 is piggybacked with, for example, the keyboard or the mouse via a shared interface 17. Thus, the distance sensor does not take up additional computer resources or require any additional source of electrical power. More distance and light sensors may be used and may be arranged in various configurations as needed.

Distance sensor 16 may be one of any of well known distance sensors in the art. In a preferred embodiment, the use of echo location with high frequency sound waves is used. As stated previously, preferably, distance sensor 16 is piggybacked with an existing computer peripheral with a shared interface. However, distance sensor 16 may be interfaced to the computer through its own interface port, such as, for example, an RS 232 serial port or USB port. Distance sensor 16 may be mounted on the monitor using an adhesive tape attachment and aimed such that the spatial volume where the distance measurements are made extends from a point very close to the monitor, for example, within 6 inches and extends out to what may be considered the farthest practical viewing distance, for example, 4 meters. Generally, optimal viewing distance is believed to be approximately 18 to 24 inches from computer monitor 12. The distance information from the sensor may be sampled, for example, once per second, and such real-time distance data is then fed directly into the computer through the interface.

In an initial step, a user 20 determines their proper viewing distance. This may be accomplished with an installation program that will ask the user to select a viewing distance. In a preferred embodiment, the optimal viewing distance would be user specific for computers used by more than one person. Preferably, the method includes displaying any one of a number of standard test patterns that are known in the art and asking the user to identify them. Preferably, the optimal viewing distance is then set slightly closer then the farthest distance at which the user is able to correctly identify the test pattern.

System 10 will preferably then notify user 20 when they are not at the proper viewing distance as measured by distance sensor 16. One way in which user 20 may be notified is by switching the display to a "screensaver" type of program when the user gets too close to the screen. Preferably, the switching algorithm used to switch to the screensaver would be intelligent and, for example, ignore momentary infrequent violations of distance limits. The type of screensaver may be selected by the user and, for example, may consist of a message indicating that the user is too close or the image may consist of a relaxing image that is pleasant to view. In any event, normal use of the computer is suspended until the user returns to the proper viewing distance or until sometime when it expires. If user 20 is a child, the screensaver may be some type of gentle reminder to move back from the computer, either visual or auditory, or it may be done with animated characters, or by motivation such as a game where the child receives points or a "gold star" if the proper viewing distance is maintained.

In accordance with another embodiment of the present invention, statistics are recorded about user 20's viewing distance, as measured by distance sensor 16. The statistics may then be monitored or analyzed in order to determine if there is a trend toward closer viewing and the length of time that the computer monitor is being viewed. This information may be used to indicate that a break is in order and, preferably, the system would notify user 20, for example, either visually or audibly.

Furthermore, the measured viewing distance may be used for a periodic test of the user's eyesight. This may be used by displaying test patterns already known in the art similar to those used above for determining optimal viewing, and "scoring" the user at some predetermined fixed distance. If user 20 scores too low on such a test, use of the computer may be inhibited. Additionally, in a preferred embodiment of the present invention, a light sensor 30 is provided that measures the level of ambient light in the user's environment and provides suggestions as to either increasing or decreasing the amount of ambient light. Light level sensor 30 may be incorporated into distance sensor 16 or may be a separate sensor all together. If it is a separate sensor, light level sensor 30 once again is preferably piggybacked with another device in the system or may have a dedicated interface, such as, for example, a RS 232 serial port.

Additionally, system 10 preferably measures a users "amplitude of accommodation," which is generally defined as the minimum distance between the eye and a viewing surface below which the surface is blurry. Such a test for amplitude of accommodation preferably is performed by having the user lean forward until the test target on the screen becomes fuzzy. As can be seen in the figures, the sensors may be incorporated into the bezel of a flat panel, LCD monitor, or any other monitor or viewing screen that may be used. While the user is at this distance where the test target has become fuzzy, the user clicks the mouse and the software measures the distance to the user via the distance sensor 16. Such a test may be performed over a period of time in order to determine the variance of the amplitude of accommodation over a period of time of use of the computer monitor.

In another embodiment of the present invention, system 10 performs color testing of the user. User 20 is preferably presented with color tests, which are known in the art, and is asked to respond to them. As with the amplitude of accommodation test, this may be performed over a period of time in order to determine the variance of the user's "interpretation" of colors over a period of time of use of the computer monitor.

System 10 also preferably monitors a user's number of times of blinking, or rate at which the user blinks their eyes. In such an embodiment, system 10 includes a small imaging sensor or camera 40 pointed at the user's face. An image analysis and pattern recognition algorithm is used to identify the user's face from other objects in a room, identify the eyes on the face and make a decision as to whether the eyes are open or not. Small digital image sensors and powerful digital signal processing circuitry is available to perform these functions and is well known in the art. Performance of the system may be improved or made user specific, for example, by having the computer user let the system take reference images of the face with their eyes both open and closed. These reference images then serve as templates in a pattern matching algorithm.

In a further embodiment of the present invention, system 10 includes testing or determining a user's visual acuity using a Landolt Ring. The technique would follow the guidelines accepted by the ophthalmic community and would be rotated randomly. Another such testing, which may commonly be referred to as rapid visual acuity testing (RVAT), would be useful for determining the visual acuity of a user at the user's working distance from the computer monitor. The visual acuity may be monitored periodically in order to determine changes over a period of time. In a preferred embodiment, user 20 would sit at their normal working distance at the computer and the screen would be blank except for arrows on an outer portion of the screen that act as indicators for a band or ring or "C" (Landolt Ring). The "C" appears on the screen as a 20/10 letter (i.e., a size of a letter that at 20 feet would appear to a user as being at 10 feet) and would slowly increase in size, for example, 20/11, 20/12. 20/13, etc., until first discernable by the user. At the point the user detects the "C," the user clicks the mouse or the enter key. The progression of the C pauses and a message appears instructing the user to identify the position of the C. If the answer is correct, the "C" is rotated randomly in two more positions. If the individual again correctly identifies the orientation of the "C," then the test is ended. Preferably, a predetermined amount of time, for example, up to five seconds for each decision, is provided.

By accurately knowing the distance of the eye from the computer, size of the "C" angular subtends, and the correct response, a software program within the computer will be able to calculate an individual's visual acuity. If improper responses are made, then the progression of size of the "C" slowly increases until the right answers are given.

By calculating the level of illumination, the testing of visual acuity may be performed at the same level of light.

The vision testing with the Landolt C patterns may be done on an LCD screen integrated into the device.

Figure 3:
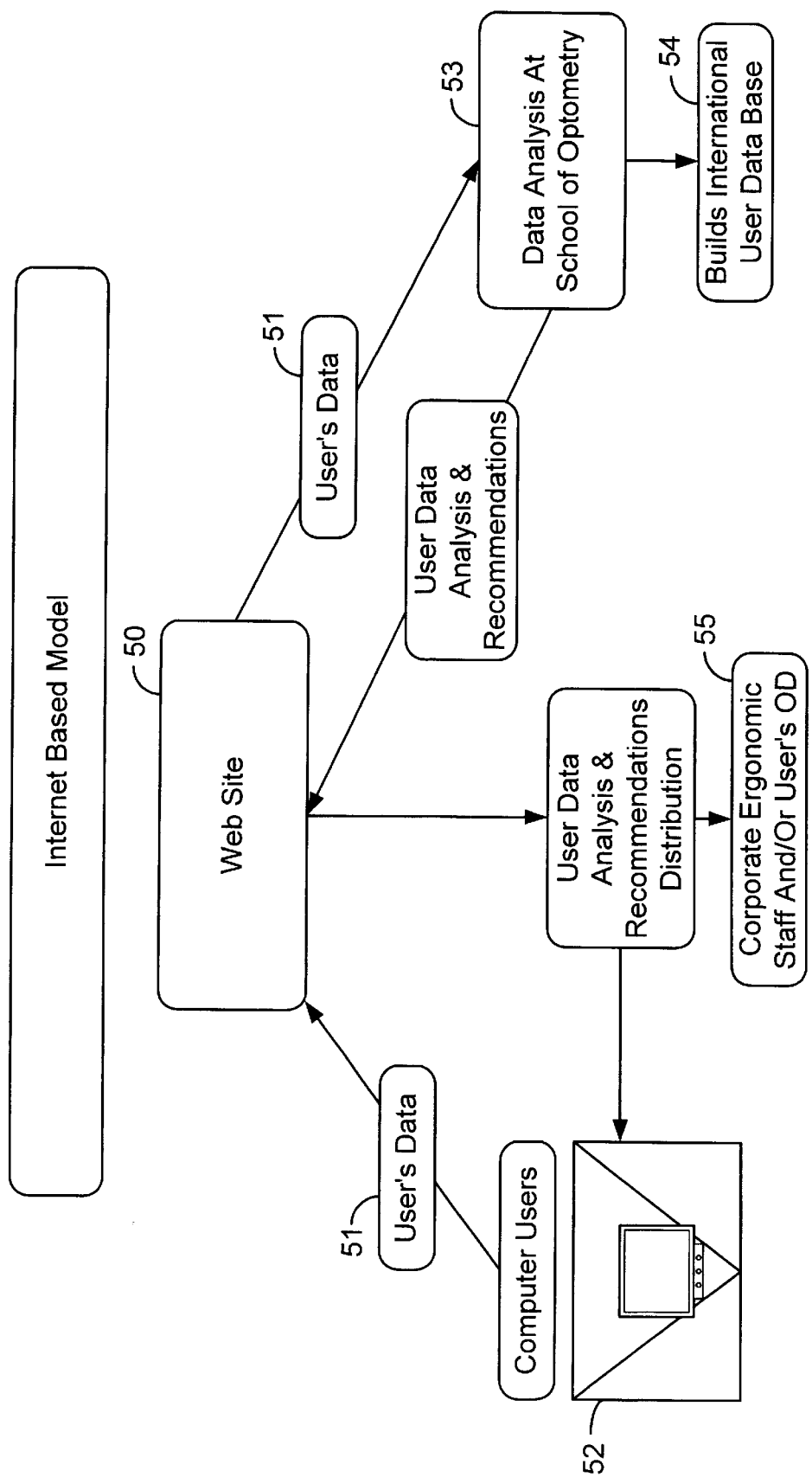
FIG. 3 is a schematic illustration of an internet-based model of a system in accordance with the present invention.

FIG. 3 illustrates a schematic illustration of an internet based model of the system in accordance with the present invention. A central website 50 is provided for receiving data 51 from a user at a local site 52 that includes computer users. The computer user's data is sent to the central website over the internet and then forwarded to an analysis location 53 that analyzes the user's data. The data analysis site also provides a central website international users' database 54 and sends back analyses and recommendations regarding the user data to the central website. The central website then distributes the data analysis and recommendations to a corporate ergonomic staff and/or users' eye care professional 55 and, if desired, to the actual user itself.

Figure 4:
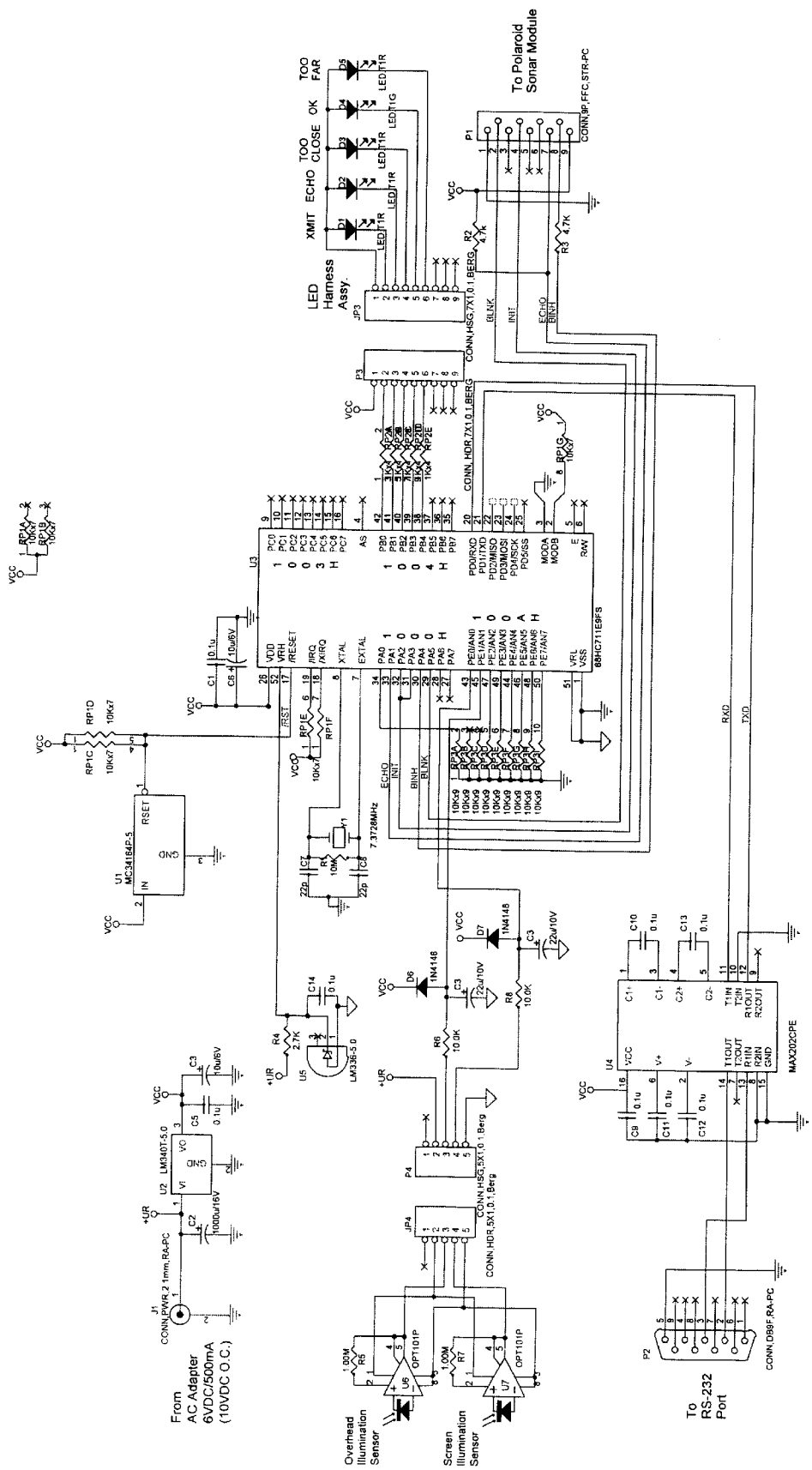
FIG. 4 is a schematic illustration of a circuit for a motherboard in accordance with the present invention.
Figure 5:
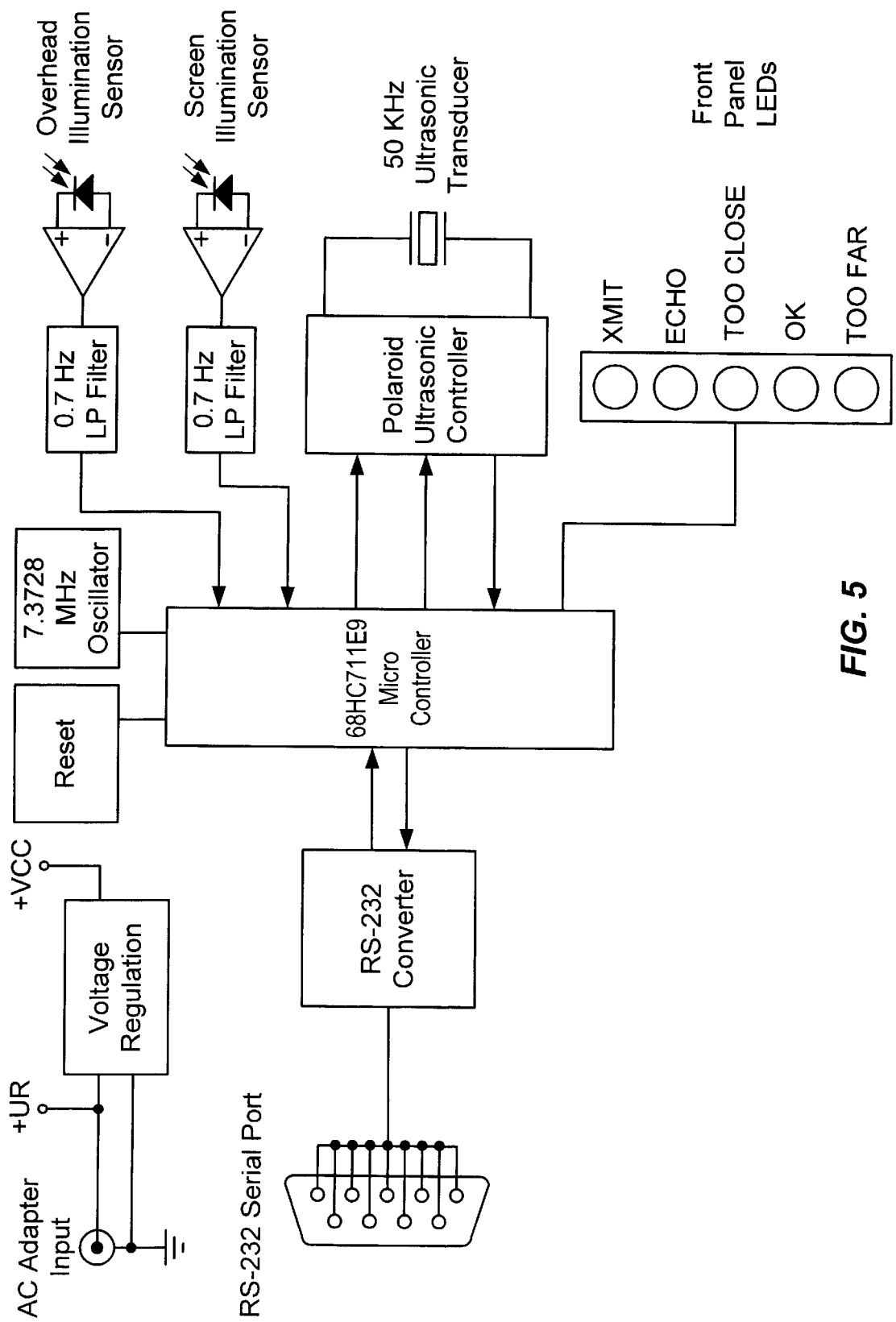
FIG. 5 is a schematic block diagram of a possible arrangement of a control system for a system in accordance with the present invention.

FIG. 4 schematically illustrates a possible circuit for a motherboard that may be included in a computer system that utilizes the present invention. FIG. 5 is an electronic block diagram of a possible control system for a system in accordance with the present invention.

The present invention may also be used for vision testing in the home for those patients who have recently undergone ocular surgery, require monitoring before surgery, are taking pharmaceuticals that may affect their vision, or have an ongoing medical problem that is vision related.

As part of vision testing, a user's central visual field may be analyzed by incorporating a dynamic "Threshold" Amsler Grid Test. A CRT or LCD monitor, a mouse and our software program preferably is used to detect and quantify any field defect (scotomas and metamorphopsia). A user will mark areas of field loss and/or aberrations using the mouse device. The contrast can be altered either electronically or graphically. This information may be transmitted via the internet for professional evaluation.

Preferably, the system resembles a laptop computer incorporating the appropriate hardware features plus a keyboard for user input and a remote input device for distance vision testing. The system also preferably includes a built-in modem configured to automatically access a website on the click of the mouse. The distance sensor may be incorporated into the mouse.

Software features preferably include user medical history, medications, and vision profiling, real time measurement of viewing distance while vision testing, adjusting test pattern size relative to viewing distance, recommendations for optimizing environmental lighting prior to vision testing, recording and tracking real time user vision performance over time, and transmitting patient information and analysis to eye care and/or medical doctor.

In the software, preferably an icon in the utility tray will be incorporated to activate onscreen directions, comments and recommendations based upon the system's data analysis. Furthermore, the software will preferably make productivity measurements by evaluating typing speed, mouse clicks, engagement time and errors. Additionally, the view size will preferably increase automatically, over time, based upon collected parameters and analyzed data provided by the software.

The system preferably allows a patient's professional care giver to prescribe the type and frequency of vision testing. Upon test completion, the patient plugs the device into a standard phone outlet to transmit the data to the website where it is stored in the patient's file and transmitted either by e-mail or fax to their doctor(s).

Preferably, the system includes three or more light meters in order to determine the source of multi-directional light relative to the user. This allows for the analysis of glare. Preferably, one separate attachable sensor is used to measure various parameters of the monitor screen. One or more of these may be attached to a retractable cable that allows it to be moved and possibly positioned facing the user's monitor to measure the brightness of the screen.

Preferably, the system includes sensors to measure ambient noise, temperature and humidity. Such information allows for proper operation of the equipment and also allows for the analysis to take into account the effects of these conditions.

While the system has been described throughout with the use of software, in an alternative embodiment, the system will be in communication with a central website. Such communication may be provided, for example, via the internet. The website would thus control the system and various parameters may be automatically changed within the system as directed from the website, such as, for example, the viewer distance from the monitor.

The system also preferably includes a leveling device for proper positioning of the individual in front of the computer. LEDs or a digital camera using a recessed LED for "sighting reference" to determine the user's position may be incorporated into the system in order to determine the correct viewing angle for the individual.

Additionally, the system preferably includes a mechanical apparatus situated under a user's monitor or incorporated into a user's desk. The apparatus automatically moves the computer monitor (including flat panel displays) in a forward or backward direction to adjust for accommodative and visual changes of the user throughout the day. The image size or view size on the user's screen will also adjust automatically in accordance with the direction of monitor display movement. The mechanical apparatus also preferably will control the height of the monitor and the viewing angle of the monitor.

The tilt of the monitor with respect to the user may be determined by placing a linear sequence of LED's behind a faceplate. The faceplate is preferably reasonably thick, for example, 0.5 inches. The LEDs shine out through holes in the faceplate. Each hole is tilted at an angle relative to substantially straight out. This means that only the LED that corresponds to the hole that is tilted at the correct angle for alignment with the viewer will be visible. Thus, the angle of tilt can be determined.

Other environmental factors such as noise, light flicker, temperature and humidity may be monitored as these may affect productivity and eyestrain. Temperature and humidity may be especially important to user's wearing contact lenses.

The typing speed and keystroke error rates may be indicative of the fatigue level of the individual user and thus, may also be monitored.

Although the invention has been described with reference to specific exemplary embodiments, it will be appreciated that it is intended to cover all modifications and equivalents within the scope of the appended claims.

What is claimed is:

1. A method of measuring ambient light level associated with use of a display by a user, comprising the steps of:
    a) providing a display, at least one light sensor and a central processing system, wherein the light sensor is positioned in a known position relative to the display and is capable of inputting information into the central processing system, and the central processing system is capable of receiving and analyzing input from the light sensor;
    b) allowing the light sensor to determine ambient light level;
    c) allowing the light sensor to input the ambient light level into the central processing system; and
    d) allowing the central processing system to receive and analyze ambient light level.

2. The method of claim 1, further comprising the step of allowing the central processing system to suggest increasing or decreasing an amount of ambient light.

3. The method of claims 1, wherein the central processing system is a computer system.

4. The method of claim 1, wherein the central processing system is accessible via Internet.

5. The method of claim 1, wherein the at least one light sensor comprises at least three light sensors.

6. A method of determining viewing distance between a user and a display and measuring ambient light level associated with use of the display, when the user is positioned in front of the display, comprising the steps of:
    a) providing a display, at least one distance sensor, at least one light sensor, and a central processing system, wherein the distance sensor is positioned in a known position relative to the display and is capable of inputting information into the central processing system, the light sensor is positioned in a known position relative to the display and is capable of inputting information into the central processing system, and the central processing system is capable of receiving and analyzing input from the distance sensor and the light sensor;
    b) allowing the distance sensor to determine the viewing distance;
    c) allowing the distance sensor to input viewing distance into the central processing system;
    d) allowing the light sensor to measure the ambient light level;
    e) allowing the light sensor to input the ambient light level into the central processing system; and
    f) allowing the central processing system to analyze viewing distance and ambient light level and to cause the results to be displayed.

7. The method of claim 6, wherein the central processing system is a computer.

8. The method of claim 6, wherein the central processing system is accessible via Internet.

9. The method of claim 6, further comprising the steps of sampling the viewing distance over time.

10. The method of claim 6, wherein the at least one distance sensor comprises more than one distance sensor.

11. The method of claim 6, wherein the at least one light sensor comprises at least three light sensors.

12. A method of measuring amplitude of accommodation of a user of a display when the user is positioned in front of the display, comprising the steps of:
    a) providing at least one distance sensor and a central processing system, wherein the distance sensor is positioned in a known position relative to the display and is capable of inputting information into the central processing system, and the central processing system is capable of receiving and analyzing input from the distance sensor;
    b) allowing the user to position the user's eye at a distance from the display when the display first becomes blurry;
    c) allowing the distance sensor to measure the viewing distance when the display first becomes blurry and inputting the viewing distance into the central processing system; and
    d) allowing the central processing system to determine the amplitude of accommodation of the user.

13. The method of claim 12, wherein the measurement is performed over a period of time to measure changes in the amplitude of accommodation over time.

14. A method of performing a color test on a user of a display, wherein the user is positioned in front of the display, comprising the steps of:
    a) providing a display and a color test on the display;
    b) providing a user-controlled input device and a central processing system, wherein the user-controlled input device is capable of inputting information into the central processing system, and the central processing system is capable of receiving and analyzing input from the user-controlled input device;
    b) allowing the imaging sensor to measure number of times the user blinks over a period of time; and
    c) allowing the central processing system to receive and analyze input from the image sensor to determine blink rate over a period of time.

15. The method of claim 14, further comprising the steps of repeating steps (c), (d) and (e) over a period of time to determine variance.

16. A method of monitoring blilnking of a user of a display when the user is positioned in front of the display, comprising the steps of:
    a) providing a display, an imaging sensor and a central processing system, wherein the imaging sensor is located in front of the user and is capable of inputting information to the central processing system, and the central processing system is capable of receiving and analyzing input from the imaging sensor;
    b) allowing the imaging sensor to measure number of times the user blinks over a period of time; and
    c) allowing the central processing system to receive and analyze input from the image sensor to determine blink rate over a period of time.

17. The method of claim 16, wherein the imaging sensor is a camera.

18. The method of claim 17, wherein the central processing system is accessible via Internet.

19. The method of claim 16, wherein the central processing system is a computer system.

20. The method of claim 16, further comprising the step of allowing the image sensor to take reference images of user with user's eyes being open and with user's eyes being closed.

21. The method of claim 20, wherein the step of displaying the visual acuity test comprises displaying a symbol and requiring the user to progressively indicate a feature in the symbol, while the feature in the symbol rotates and the symbol changes in size.

22. The method of claim 21, wherein the symbol is a band, a ring or a letter "C".

23. The method of claim 21, wherein the symbol is a letter "C," wherein the letter "C" comprises an opening, and the feature in the symbol is the opening.

24. The method of claim 21, wherein the method comprises providing a software program, wherein the software program is capable of performing the steps comprising of:
   a) causing the display to display a letter "C" as a 20/10 letter;
   b) increasing the size of the letter "C" until it is discernible to the user;
   c) detecting a response by the user when user discerns the letter "C";
   d) requiring user to respond by identifying correct position of the letter "C";
   e) accepting user's response;
   f) rotating the letter "C" when user identifies the correct position of the letter "C";
   g) repeating steps (d) and (e);
   h) allowing the central processing system to analyze user's responses to determine the user's visual acuity;
   wherein the size of the letter "C" is increased progressively each time if user is unable to identify the correct position of the letter "C," until a correct response is obtained.

25. A method of determining a user's visual acuity, when the user is positioned in front of a display, comprising the steps of:
   a) providing at least one light sensor, a display, and a central processing system, wherein the light sensor is positioned in a known position relative to the display and is capable of inputting information into the central processing system, and the central processing system is capable of receiving and analyzing input from the light sensor;
   b) allowing the display to display a visual acuity test;
   c) allowing the light sensor to measure ambient light level and to input the ambient light level to the central processing system;
   d) allowing the user to respond to the visual acuity test and to input the response to the central processing system; and
   e) allowing the central processing system to analyze the user's acuity test response.

26. The method of claim 25, further comprising the steps of: providing at least one distance sensor, wherein the distance sensor is positioned in a known position relative to the display and is capable of inputting information into the central processing system, and the central processing system is capable of receiving and analyzing input from the distance sensor, and allowing the distance sensor to determine the viewing distance and to input the viewing distance into a central process system.

27. The method of claim 25, wherein the method of determining a user's visual acuity is performed over a period of time at the same ambient light level.

28. The method of claim 25, wherein the central processing system is a computer system.

29. The method of claim 25, wherein the central processing system is accessible via Internet.

30. The method of claim 25, wherein the user is a patient who has a vision-related medical condition.

31. A method of determining glare associated with use of a display by a user, comprising the steps of:
   a) providing a display, a plurality of light meters, and a central processing system, wherein the light meters are capable of detecting source of multi-directional light relative to the user and of inputting information to the central processing system, and the central processing system is capable of receiving and analyzing input from the light meters;
   b) allowing the light meters to detect light sources and inputting light source information to the central processing system; and
   c) allowing the central processing system to receive and analyze input from the light meters to determine glare.

32. The method of claim 31, wherein the central processing system is a computer system.

33. The method of claim 31, wherein the central processing system is accessible via Internet.

34. A method of monitoring a patient's vision remotely comprising the steps of:
   a) allowing the patient to perform a vision test using a display at a remote site;
   b) allowing the patient to input information from the vision test into a central processing system;
   c) allowing the input information to be analyzed; and
   d) allowing results from the analysis to be displayed.

35. The method of claim 34, where in the subject is selected from the group consisting of: one who has undergone ocular surgery, one who requires monitoring before surgery, one who is taking medication that may affect vision, and one who has an ongoing medical problem that is vision related.

36. A method of measuring productivity of a user when user is positioned in front of a display, comprising the steps of:
   a) providing a display, at least one distance sensor, at least one light sensor, at least one imaging sensor and a central processing system, wherein the distance sensor, the light sensor and the imaging sensor are each capable of inputting information into the central processing system, and the central processing system is capable of receiving and analyzing input from the distance sensor, the light sensor and the imaging sensor;
   b) allowing the sensors to detect typing, mouse clicks, and blinking of the user over a period of time;
   c) allowing the central processing system to analyze typing speed, mouse clicks, blink rate and time elapsed to determine productivity.

37. A software program for performing a visual acuity test of a user, wherein the software program is configured to perform the steps comprising of:

a) causing a display to display a letter "C" as a 20/10 letter;
b) increasing the size of the letter "C" until it is discernible to the user;
c) detecting a response by the user when user discerns the letter "C";
d) requiring the user to respond by identifying correct position of the letter "C";
e) accepting the user's response;
f) rotating the letter "C" when user identifies the correct position of the letter "C";
g) repeating the steps (d), (e) and (f
h) allowing the central processing system to analyze user's responses to determine the user's visual acuity;
wherein the size of the letter "C" is increased progressively each time if user is unable to identify the correct position of the letter "C," until a correct response is obtained.

38. A system for monitoring use of a display by a user when the user is position in front of the display, comprising:
a) a display that is capable of display information from inputted into or from a central processing system;
b) at least one distance sensor that is capable of measuring viewing distance and inputting information into the central processing system;
c) at least one light sensor that is capable of detecting ambient light level and is capable of inputting information into the central processing system; and
d) the central processing system that is capable of receiving. and analyzing information received from the distance sensor and light sensor.

39. The system of claim 38, further comprising a mechanical apparatus that is capable of moving the display in one, two, or three dimensions in response to input from the central processing system.

40. The system of claim 38, further comprising at least one sensor selected from the sting of a noise sensor, a temperature sensor, a humidity sensor and an imaging being capable of inputting information into the central processing system.

41. The system of claim 38, wherein the 3 light sensors are positioned to determine source of multidirectional light relative to the user.

42. The system of claim 38, further comprising an image sensor, wherein the image sensor is capable of inputting information into the central processing system.

43. The system of claim 42, wherein the image sensor is a camera.

44. The system of claim 42, wherein the image sensor is capable of detecting blinking over a period of time and the central processing system is capable of analyzing blink rate.

45. The system of claim 38, wherein the mechanical apparatus provides for automatically moving the display to adjust for accommodative and visual changes of the user.

* * * * *

UNITED STATES PATENT AND TRADEMARK OFFICE
CERTIFICATE OF CORRECTION

PATENT NO. : 6,592,223 B1
DATED : July 15, 2003
INVENTOR(S) : Stern et al.

It is certified that error appears in the above-identified patent and that said Letters Patent is hereby corrected as shown below:

Column 8,
Lines 35-49, claim 14 should read as follows:
14. A method of performing a color test on a user of a display, wherein the user is positioned in front of the display, comprising the steps of:
a) providing a display and a color test on the display;
b) providing a user-controlled input device and a central processing system, wherein the user controlled input device is capable of inputting information into the central processing system, and the central processing system is capable of receiving and analyzing input from the user-controlled input device;
c)    allowing the user to perform the color test;
d)    allowing the user to input a response into the central processing system; and
e)    allowing the central processing system to analyze the response.
Lines 54-67, claim 16 should read as follows:
16. A method of monitoring blinking of a user of a display when the user is positioned in front of the display, comprising the steps of:
a) providing a display, an imaging sensor and a central processing system, wherein the imaging sensor is located in front of the user and is capable of inputting information to the central processing system, and the central processing system is capable of receiving and analyzing input from the imaging sensor;
b) allowing the imaging sensor to measure number of times the user blinks over a period of time;
c) allowing the central processing system to receive and analyze input from the image sensor to determine blink rate over a period of time.

Column 9,
Lines 3-4, claim 18 should read as follows:
18. The method of claim 16, wherein the central processing system is accessible via internet.
Lines 11-15, claim 21 should read as follows:
21. The method of claim 25, wherein the step of displaying the visual acuity test comprises displaying a symbol and requiring the user to progressively indicate a feature in the symbol, while the feature in the symbol rotates and the symbol changes in size.

Column 11, line 21 - Column 12, line 3,
Claim 38 should read as follows:
38. A system for monitoring use of a display by a user when the user is positioned in front of the display, comprising:
a) a display that is capable of displaying information inputted into or from central processing system;

UNITED STATES PATENT AND TRADEMARK OFFICE
CERTIFICATE OF CORRECTION

PATENT NO. : 6,592,223 B1
DATED : July 15, 2003
INVENTOR(S) : Stern et al.

It is certified that error appears in the above-identified patent and that said Letters Patent is hereby corrected as shown below:

Column 11, line 21 - Column 12, line 3 (cont'd),
b) at least one distance sensor that is capable of measuring viewing distance and inputting information into the central processing system;
c) at least one light sensor that is capable of detecting ambient light level and is capable of inputting information into the central processing system;
d) the central processing system that is capable of receiving and analyzing information received from the distance sensor and light sensor.

Column 12,
Lines 8-12, claim 40 should read as follows:
40. The system of claim 38, further comprising at least one sensor selected from the group consisting of a noise sensor, a temperature sensor, a humidity sensor and an imaging sensor, each being capable of inputting information into the central processing system.
Lines 13-15, claim 41 should read as follows:
41. The system of claim 38, wherein the system comprises 3 light sensors and the 3 light sensors are positioned to determine source of multidirectional light relative to the user.
Lines 24-26, claim 45 should read as follows:
45. The system of claim 38, wherein the system further comprises a mechanical apparatus and the mechanical apparatus provides for automatically moving the display to adjust for accommodative and visual changes of the user.

Signed and Sealed this

Twenty-sixth Day of April, 2005

JON W. DUDAS
*Director of the United States Patent and Trademark Office*